US006042546A

United States Patent [19]

Bae

[11] Patent Number: 6,042,546

[45] Date of Patent: Mar. 28, 2000

[54] ELEMENT ARRANGING STRUCTURE FOR TRANSDUCER ARRAY FOR FORMING THREE-DIMENSIONAL IMAGES AND ULTRASONIC THREE-DIMENSIONAL IMAGING APPARATUS ADOPTING THE SAME

[75] Inventor: Moo-Ho Bae, Seoul, Rep. of Korea

[73] Assignee: Medison Co., Ltd., Rep. of Korea

[21] Appl. No.: 08/889,248

[22] Filed: Jul. 8, 1997

[30] Foreign Application Priority Data

Jul. 8, 1996 [KR] Rep. of Korea ....................... 96-27484

[51] Int. Cl.[7] ........................................................ A61B 8/00

[52] U.S. Cl. .......................... 600/447; 600/459; 128/916

[58] Field of Search .................................... 600/437, 443, 600/447; 128/459, 910

[56] References Cited

U.S. PATENT DOCUMENTS

| | | | |
|---|---|---|---|
| 3,953,825 | 4/1976 | Kino et al. | 73/626 |
| 4,893,629 | 1/1990 | Lewsi | 600/443 |
| 5,305,756 | 4/1994 | Entrekin et al. | 600/459 |
| 5,329,496 | 7/1994 | Smith | 600/459 |
| 5,417,219 | 5/1995 | Takamizawa et al. . | |
| 5,546,946 | 8/1996 | Souquet | 600/459 |
| 5,549,111 | 8/1996 | Wright et al. | 600/443 |
| 5,553,035 | 9/1996 | Seyed-Bolorforosh et al. | 600/459 |
| 5,671,746 | 9/1997 | Dreschel et al. | 600/459 |
| 5,678,554 | 10/1997 | Hossoch et al. | 600/459 |
| 5,706,816 | 1/1998 | Mochizaki et al. | 628/916 |
| 5,792,058 | 8/1998 | Lee et al. | 600/459 |
| 5,906,580 | 5/1999 | Kline-Schodes et al. | 600/437 |

*Primary Examiner*—Francis J. Jaworski
*Attorney, Agent, or Firm*—Dilworth & Barrese

[57] ABSTRACT

An element arranging structure for a transducer array to form three-dimensional images of an object from the surface shape of the object is provided. The transducer array includes a plurality of sub-elements each having a respectively different center frequency. The transducer array, with sub-elements, enable ultrasonic three-dimensional image formation by analyzing the frequency spectrum of received ultrasonic echo signals to discern a plurality of targets, and determining the position of the elevational direction for each target as a peak frequency.

6 Claims, 8 Drawing Sheets

ELEMENT ARRANGING STRUCTURE FOR TRANSDUCER ARRAY FOR FORMING THREE-DIMENSIONAL IMAGES AND ULTRASONIC THREE-DIMENSIONAL IMAGING APPARATUS ADOPTING THE SAME

BACKGROUND OF THE INVENTION

The present invention relates to an ultrasonic three-dimensional imaging, and more particularly, to an element arranging structure for a transducer array to form three-dimensional images of an object from a shape of the surface of the object, that is, three-dimensional images in consideration of an elevational direction and an ultrasonic imaging apparatus adopting the same.

Ultrasonic imaging systems display the sectional structure of a human body using an ultrasonic wave, which are widely used in medical fields such as the internal department, pediatrics, obstetrics and gynecology. In particular, a B-mode imaging apparatus which can observe the sectional structure of a human body and an imaging apparatus which can provide the blood stream information in a human body as images using an ultrasonic Doppler phenomenon caused when being reflected from a moving object, are the most widely used. An ultrasonic three-dimensional imaging apparatus providing such ultrasonic information into three-dimensional images is recently under development.

FIG. 1 is a view for explaining a method in which beams are focussed in a transducer of a general ultrasonic two-dimensional imaging apparatus.

As shown in FIG. 1, a general ultrasonic two-dimensional imaging apparatus focuses ultrasonic beams on a scan line via a transducer array having elements which are arranged in line and moves the ultrasonic beams on a plane based on a scan line, to thereby form the section of an object which crosses with the plane into an image. Here, a reaching time of an ultrasonic pulse incident to a transducer array varies according to the position of each element. That is, it takes more time for a far element from the center of the transducer array to receive an ultrasonic echo signal than a near element does. Therefore, the ultrasonic imaging apparatus performs an ultrasonic focusing operation so that ultrasonic echo signals received via the elements of a transducer are in phase. Such a focusing operation can be performed at the time of transmission. However, it is preferable that a focusing operation is performed at the time of reception in order to achieve dynamic focusing. Such dynamic focusing dynamically transforms a delay time according to a scanning operation of the ultrasonic beams to thereby trace the position where the ultrasonic echo signal returns. The general ultrasonic imaging apparatus maintains a fixed focal point by using an acoustic lens and properly adjusting a geometrical array of the elements in the case when ultrasonic signals are focussed in an elevational direction. This method can work a discriminative force in a lateral and elevational directions of the elements. Also, a transducer 10 generates an ultrasonic signal in the form of a pulse wave not a continuous wave for an axial discriminative force.

FIG. 2 shows a general ultrasonic two-dimensional imaging apparatus having the transducer 10 of FIG. 1. A pulse voltage generated from a transmitter 5 is applied to each element of the transducer 10. The elements generate an ultrasonic beam according to the pulse voltage. Here, the pulse voltage is made to have a respective time delay according to elements which differ in their position, so that a lateral transmit focusing is accomplished. The ultrasonic pulse is propagated into an object and is reflected from a target of the object to then be again incident to the elements of the transducer 10. The elements transform the returned ultrasonic echo signal into an electrical signal. An amplifier 20 amplifies the ultrasonic echo signal received from the transducer 10. A time gain compensator (TGC) 30 varies the gain of a signal applied from the amplifier 20 according to a time and compensates an attenuation due to an ultrasonic reception distance. A beam former 40 time-delays the input signals differently from each other, and then adds all the time-delayed signals, to thereby perform a lateral receive focusing. Here, the beam former 40 varies an amount of time delay for every instant to perform the receive focusing. An envelop detector 50 receives a signal passed through the beam former 40 to perform an envelop detection. A function transformer 60 compresses the envelop detection result into a predetermined function. An analog-to-digital converter/digital scan converter 70 converts the input signal into a digital signal and performs a digital scan conversion, to then be displayed on a display 80.

U.S. Pat. No. 5,305,756 discloses a three-dimensional imaging method which can use most of the two-dimensional ultrasonic imaging apparatus without any substantial change, by improving only a transducer. Therefore, the above U.S. patent technology has the advantage of realizing an image on a real time basis, and implementing an ultrasonic image diagnostic apparatus at low cost.

Referring to FIG. 3, the three-dimensional imaging apparatus disclosed in the above U.S. Pat. No. 5,305,756 will be described briefly.

Lateral and axial focusing methods for beam forming are same as a general two-dimensional imaging method shown in FIG. 1, but differ from an elevation focusing method. The elevation focusing method spreads a beam broadly, that is, fans out a beam, in contrast to that of FIG. 1, with a result that the beam is focused on one surface of an object (see U.S. Pat. No. 5,417,219. Then, the focused surface is moved in the direction perpendicular to the surface to scan a three-dimensional space. Here, when a focusing is performed ideally so that an ultrasonic beam is positioned on the only single plane, a method for forming a three-dimensional image of an object will be described with reference to FIGS. 4A and 4B.

In FIG. 4A, it is assumed that an ultrasonic beam exists on the only plane PQRS. Characters A, B, C and D denote arbitrary points on a line PR. It is also assumed that characters A', B', C' and D' denote points existing on the surface of the object at the same distance as a distance from the center of a line PQ to the points A, B, C and D, respectively. It is further also assumed that an ultrasonic reflection is identically realized at all the points on the surface of the object. An ultrasonic echo signal returned from the point D' is led earlier in time and larger in size than those from the points A', B' and C'. The reason is because since the point D' is relatively closer to the transducer 10 than the other points, and the surface of the object near the point D' is substantially perpendicular to an ultrasonic travelling direction, more ultrasonic echo signals return to the transducer. The ultrasonic echo signal returns in sequence of the points D', A', B' and C' in view of time. However, as shown in FIG. 4B, The reason why an ultrasonic echo signal which is received at the point A' is feebler than that of the point D' is because an ultrasonic beam is scattered and few signals return to the transducer since the surface of the object at the point A' is substantially horizontal with respect to an ultrasonic travelling direction. That is, the ultrasonic echo signal returning to the transducer 10 is feeblest at the point A' and strongest at the point D'. The farther a distance between the transducer and the object, the more broadly the ultrasonic beam becomes spread. As a result, the size of the ultrasonic echo signal becomes smaller. However, since it can be seen how the ultrasonic echo signal will become smaller, it is possible to compensate a reduction in size according to time.

The above-described ultrasonic three-dimensional imaging apparatus obtains an image of a straight line when one plane is scanned, and performs a mapping for brightness of the points on the straight line with an intensity of the ultrasonic echo signal. The intensity of the ultrasonic echo signal is determined by an ultrasonic reflectivity of an object and a slope of the surface of an object in an ultrasonic travelling direction. After scanning one plane, the scanned plane is moved little by little in the lateral direction and then the above-described operation is repeated. Accordingly, a three-dimensional image representing a shape of the surface of the object is obtained by gathering thus-obtained several straight line images.

Meanwhile, although the above-described imaging method can very simply form the shape of the surface of the object into a three-dimensional image, an image being different from a real shape of an image is obtained under the circumstance of FIGS. 5A, 5B and 6.

FIGS. 5A, 5B and 6 are views for explaining problems of a conventional ultrasonic three-dimensional imaging apparatus.

FIG. 5A shows a case when two objects having the same shape are parallel with each other. FIG. 5B shows a case when one of the above two objects is reversed with respect to the elevational direction. Here, if an object is reversed on the basis of a lateral-axial plane passing through the center of a transducer, the same shape is obtained in both cases of FIGS. 5A and 5B. In other words, the conventional ultrasonic three-dimensional imaging apparatus can measure only a distance between the transducer and the scanned surface of the object, and obtains the same three-dimensional image in both cases shown in FIGS. 5A and 5B because there is no information about which is a point reflected from the actual object.

Another problem will be described with reference to FIG. 6. There is no problem in case when a line that a scan plane and an object intersects with each other is unique (see FIGS. 4A and 4B). As shown in FIG. 6, an object is completely included in the scan plane, and thus several lines intersect with the object and the scan plane, in which a brightness corresponding to a sum of the image lines is obtained. That is, the point A is assigned with a brightness corresponding to a sum of echo signals returning from points A' and A", and the same is also applied to the case with points B and C. That is, in FIG. 6, the upper surface and the lower surface of an object are never distinguished on a screen. As a result, a shape different from that of an actual object can be displayed on a screen.

SUMMARY OF THE INVENTION

To solve the above problems, it is an object of the present invention to provide an element arranging method for a transducer array in which sub-elements having respectively different center frequencies are expressed as a function of angle of an elevational direction, so as to discern a plurality of targets which are located at the same distance.

It is another object of the present invention to provide an ultrasonic three-dimensional imaging apparatus for use in a transducer array having a plurality of sub-elements having a respectively different center frequency, by analyzing a frequency spectrum of a received ultrasonic echo signal to discern a plurality of targets, and determining the position of an elevational direction at each target as a peak frequency.

To accomplish the above object of the present invention, there is provided an element arranging structure for a transducer array, for using in an ultrasonic three-dimensional imaging, in which a plurality of sub-elements having a respectively different center frequency are arranged at the position of each element on a plane determined by an elevational direction and a scanning direction in the form of a variable ultrasonic launching direction of each sub-element.

To accomplish another object of the present invention, there is provided an ultrasonic three-dimensional imaging apparatus comprising:

- a transducer array including sub-elements having a respectively different center frequency; an ultrasonic signal processor for receiving and focusing an ultrasonic echo signal received from an object via a predetermined time delay and converting it into a digital ultrasonic signal; and a frequency analysis unit for analyzing a frequency spectrum of the digital ultrasonic signal applied from the ultrasonic signal processor, gathering spatial image information, and signal-processing and displaying the gathered image information.

BRIEF DESCRIPTION OF THE DRAWINGS

The present invention will be described in more detail with reference to the accompanying drawings in which.

DETAILED DESCRIPTION OF THE PREFERRED EMBODIMENT

A preferred embodiment of the present invention will be described in detail with reference to the accompanying drawings.

Figure 7:
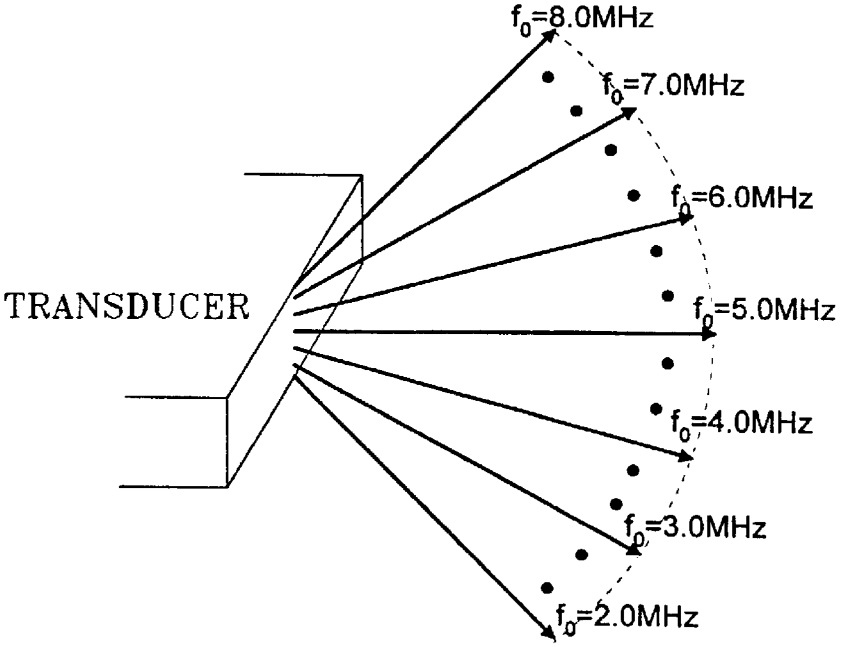
FIGS. 7 and 8 show a transducer in which sub-elements having a respectively different center frequency in the elevational direction are arranged in an element according to a preferred embodiment of the present invention.
Figure 8:
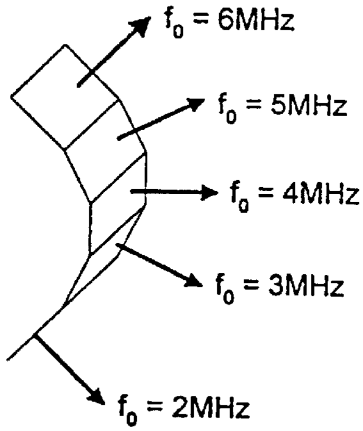

FIGS. 7 and 8 show a transducer in which sub-elements having a respectively different center frequency in the elevational direction are arranged in sequence of a frequency size in an element according to a preferred embodiment of the present invention. An element forming a transducer array includes a plurality of sub-elements. The sub-elements are electrically connected in parallel and operates as an element. The transducer array of the present invention includes a number of the sub-elements having a respectively different center frequency, to make a beam whose center frequency continuously or gradually varies in the elevational direction.

Figure 1:
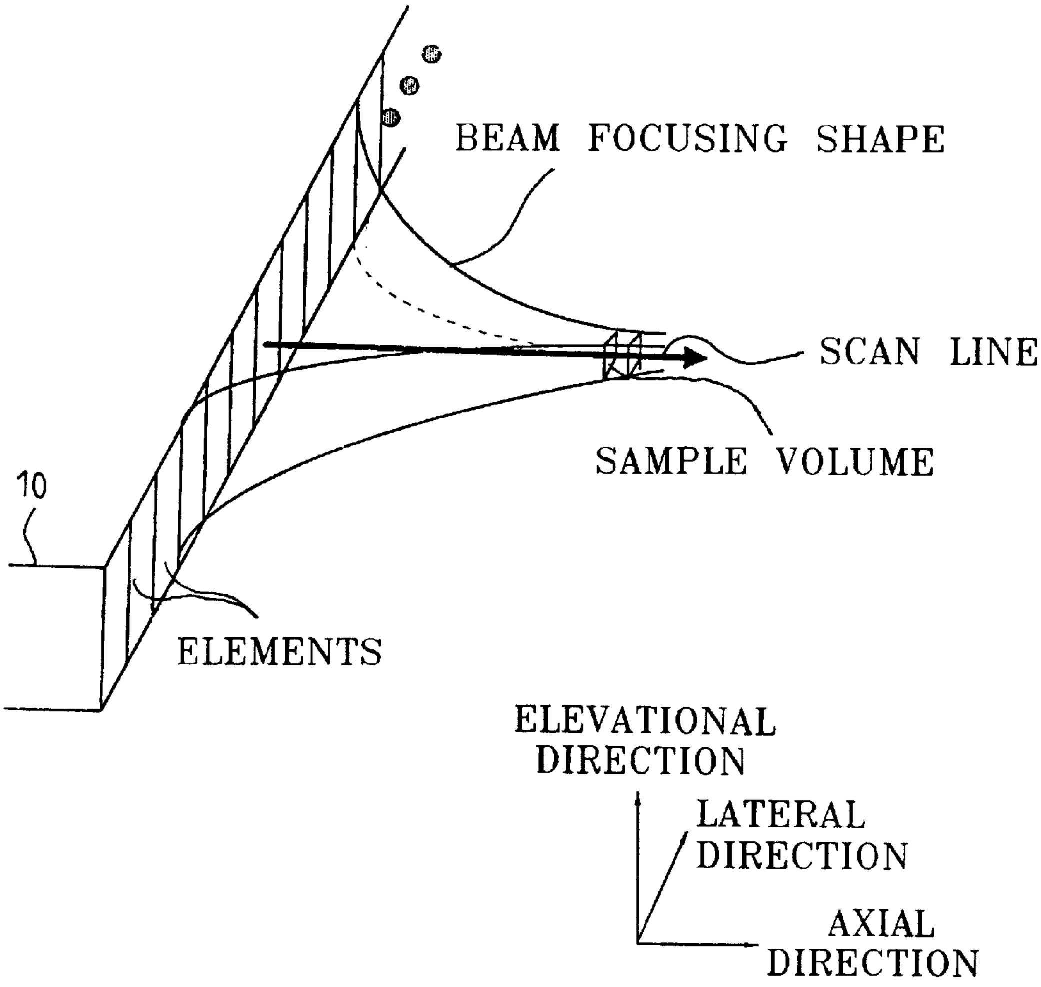
FIG. 1 (PRIOR ART)
FIG. 1 is a view for explaining a method in which beams are focussed in a transducer of a general ultrasonic two-dimensional imaging apparatus.
Figure 2:
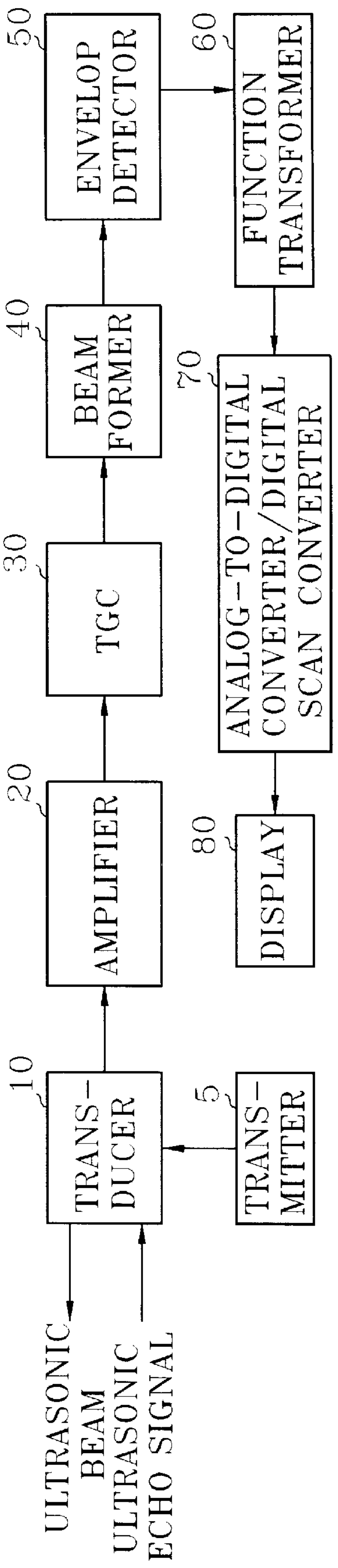
FIG. 2 (PRIOR ART)
FIG. 2 shows a general ultrasonic two-dimensional imaging apparatus having a transducer 10 of FIG. 1.
Figure 3:
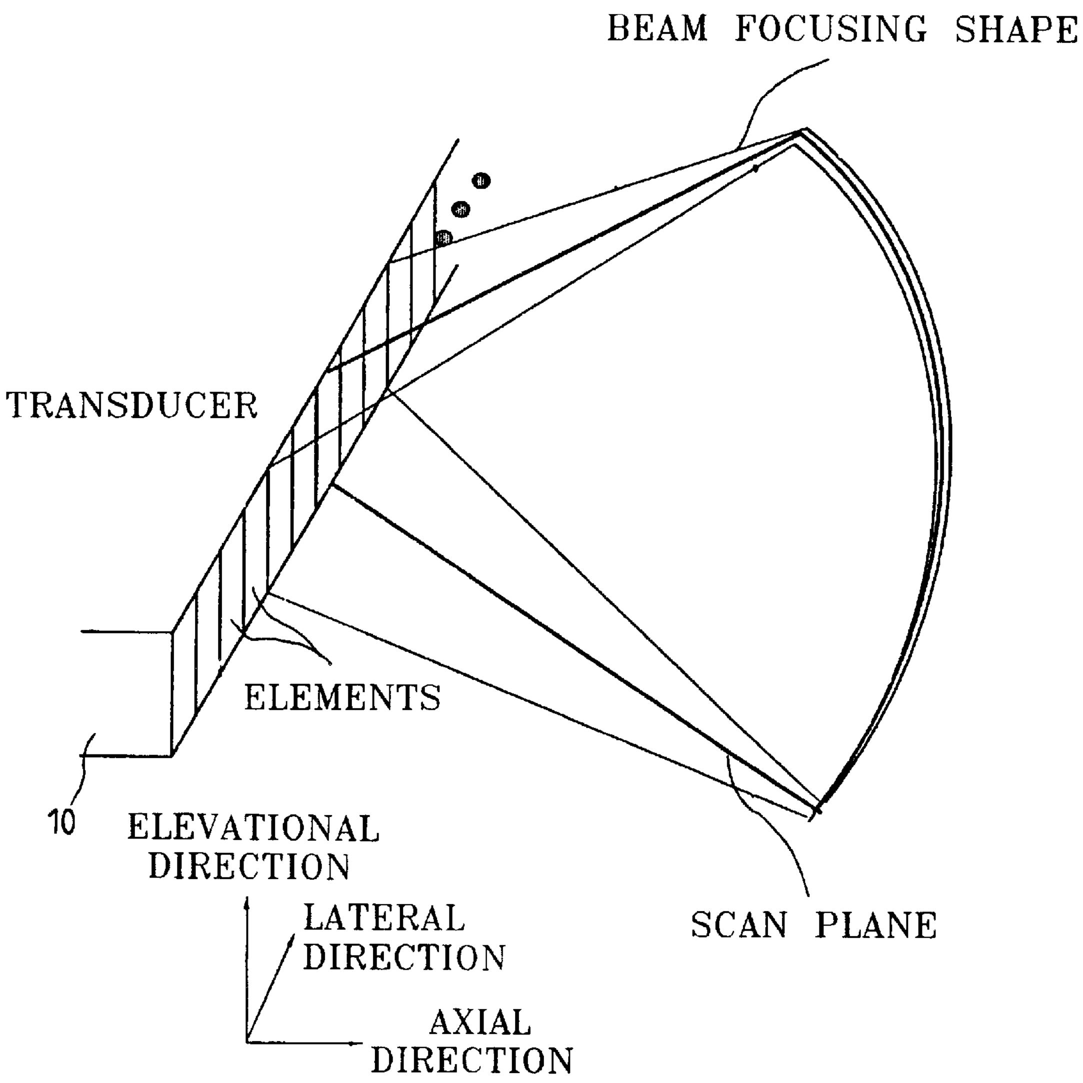
FIG. 3 (PRIOR ART)
FIG. 3 shows a beam focusing shape for explaining a conventional three-dimensional imaging method.
Figure 4A:
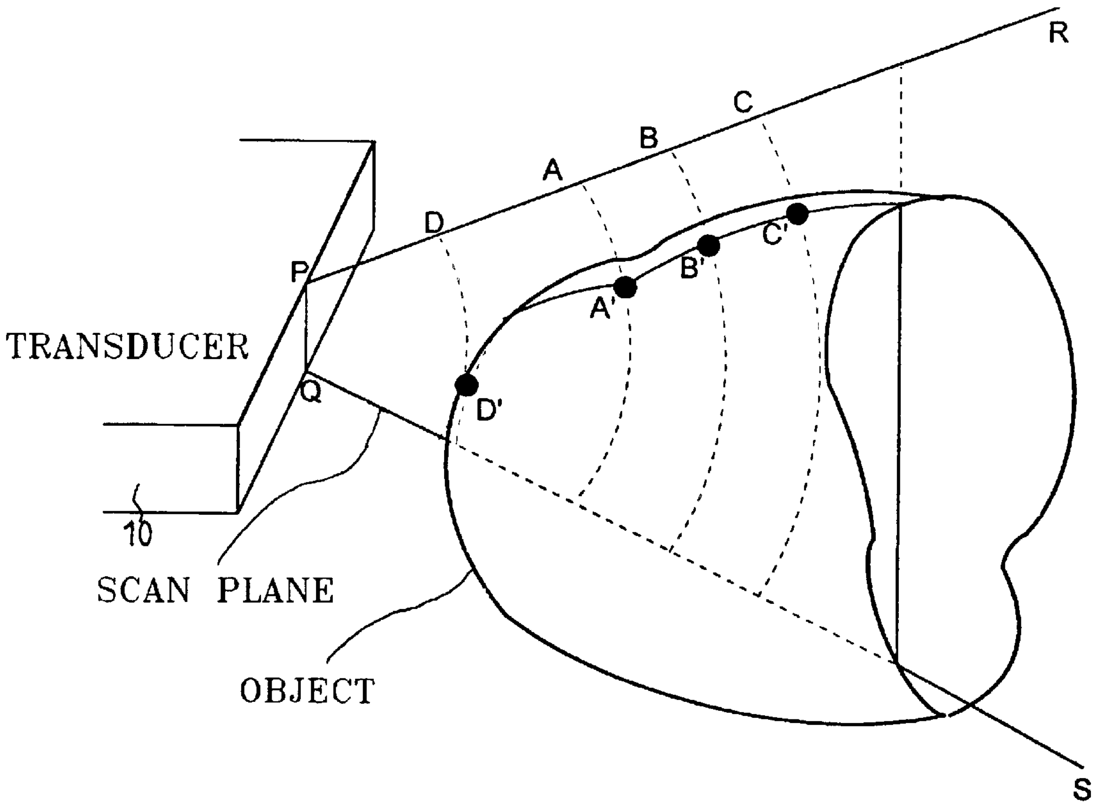
FIG. 4A (PRIOR ART)
FIGS. 4A and 4B are views showing a three-dimensional imaging method in the case when an ultrasonic beam is positioned on an only one plane due to an ideal focusing.
Figure 4B:
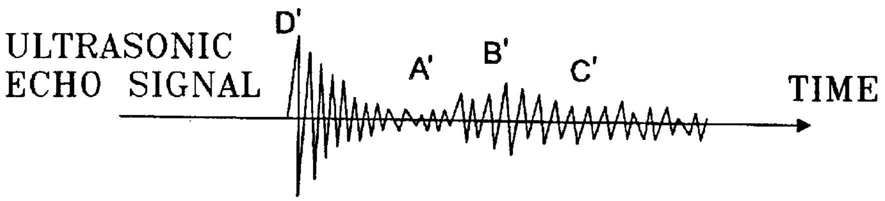
FIG. 4B (PRIOR ART)
Figure 5A:
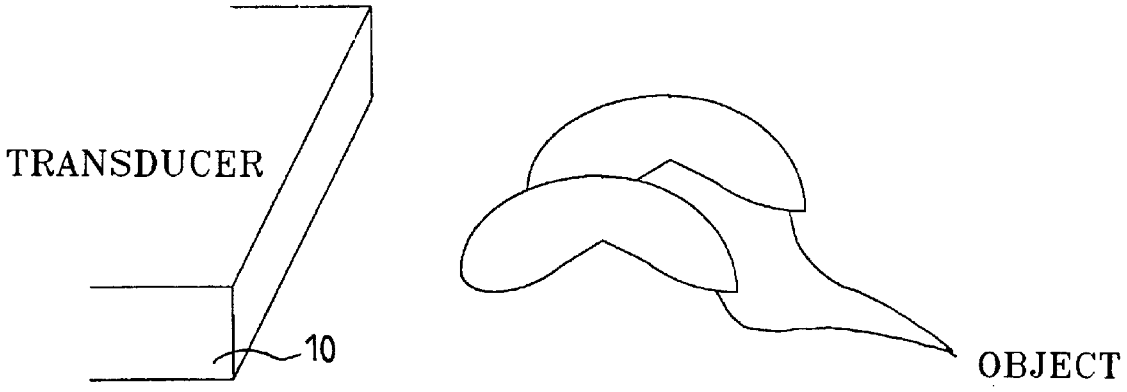
FIG. 5A (PRIOR ART)
FIGS. 5A, 5B and 6 are views for explaining problems of a conventional ultrasonic three-dimensional imaging apparatus.
Figure 5B:
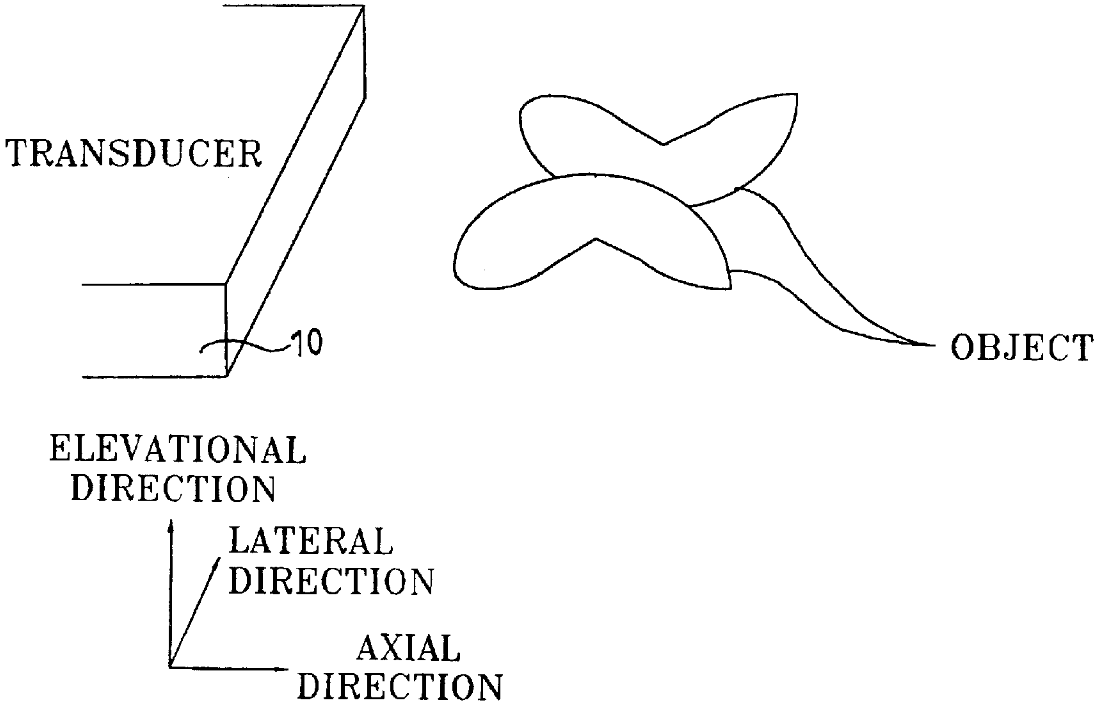
FIG. 5B (PRIOR ART)
Figure 9:
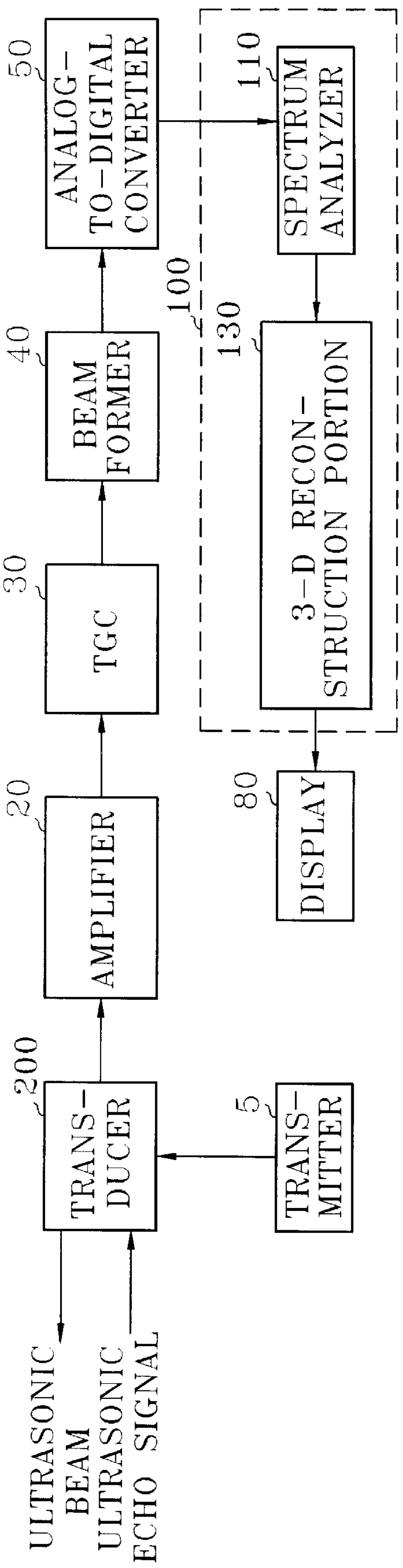
FIG. 9 is a block diagram showing an ultrasonic three-dimensional imaging apparatus according to a preferred embodiment of the present invention.

FIG. 9 is a block diagram showing an ultrasonic three-dimensional imaging apparatus using a transducer array shown in FIG. 7 according to the present invention. The present invention apparatus includes a transducer array 200 in which sub-elements having a respectively different center frequency form an element. Also, the present invention apparatus includes the same portions 20 through 50 as those of the ultrasonic two-dimensional imaging apparatus shown in FIG. 2, and further includes a frequency analyzer 100. The frequency analyzer 100 includes a spectrum analyzer 110 for analyzing a frequency spectrum of an ultrasonic beam applied from an analog-to-digital converter 50 and a three-dimensional (3-D) reconstruction portion 130 for calculating three-dimensional image information so as to be displayed in a user's desired form.

The ultrasonic three-dimensional imaging apparatus according to the present invention forms an image when a number of targets exist on a scan plane using a transducer array having sub-elements, in which a distance reaching each target can be seen using an ultrasonic echo signal return time as in the conventional ultrasonic image diagnostic apparatus. An angle between a line connecting from a target to the center of the transducer and a lateral-axial plane can be seen via a frequency spectrum of an echo signal.

Figure 10A:
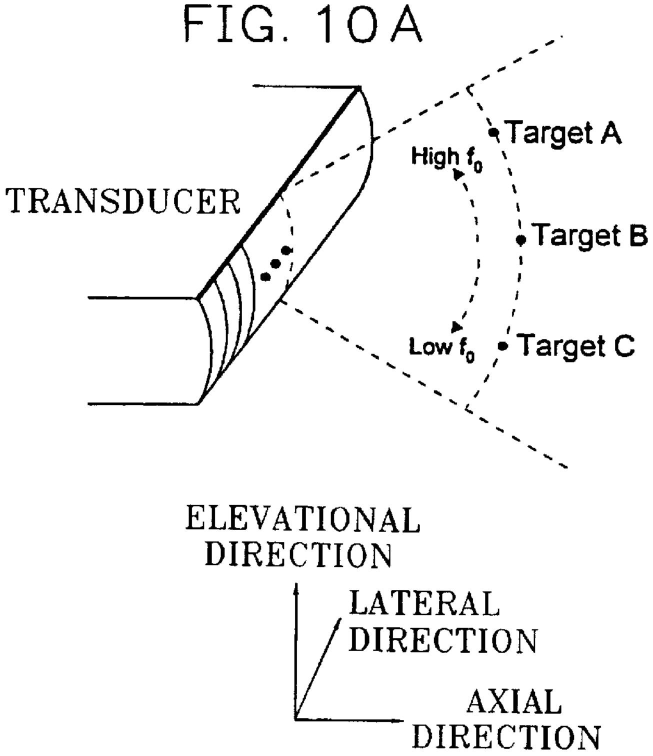
FIGS. 10A through 10C are views for explaining a method embodying an ultrasonic three-dimensional imaging apparatus according to a preferred embodiment of the present invention.
Figure 10B:
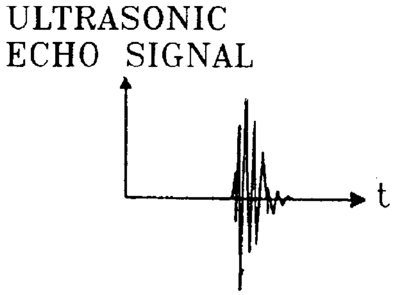
Figure 10C:
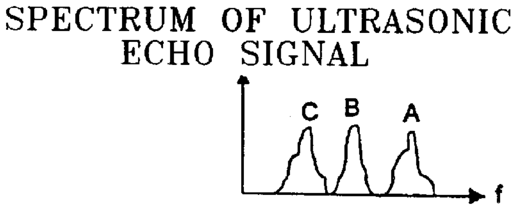

FIGS. 10A through 10C are views for explaining a method embodying an ultrasonic three-dimensional imaging apparatus shown in FIG. 9 according to a preferred embodiment of the present invention. FIG. 10A shows a method in which an image is formed from an object having three targets A, B and C which are located at equal distances. When an image is formed from the object having three targets as shown in FIG. 10A, the three targets in an identical time domain can not discerned from each other by means of a ultrasonic echo signal, as shown in FIG. 10B. However, the three targets A, B and C can be respectively distinguished at a frequency spectrum of the ultrasonic echo signal as shown in FIG. 10C. In this case, it can be seen that a target exists in every peak value of the spectrum, and that the position of the elevational direction of the target can be determined by the frequency of the peak value. When such information is obtained, an ultrasonic echo signal reflected from a three-dimensional spatial coordinate can be obtained on a real time basis.

Figure 6:
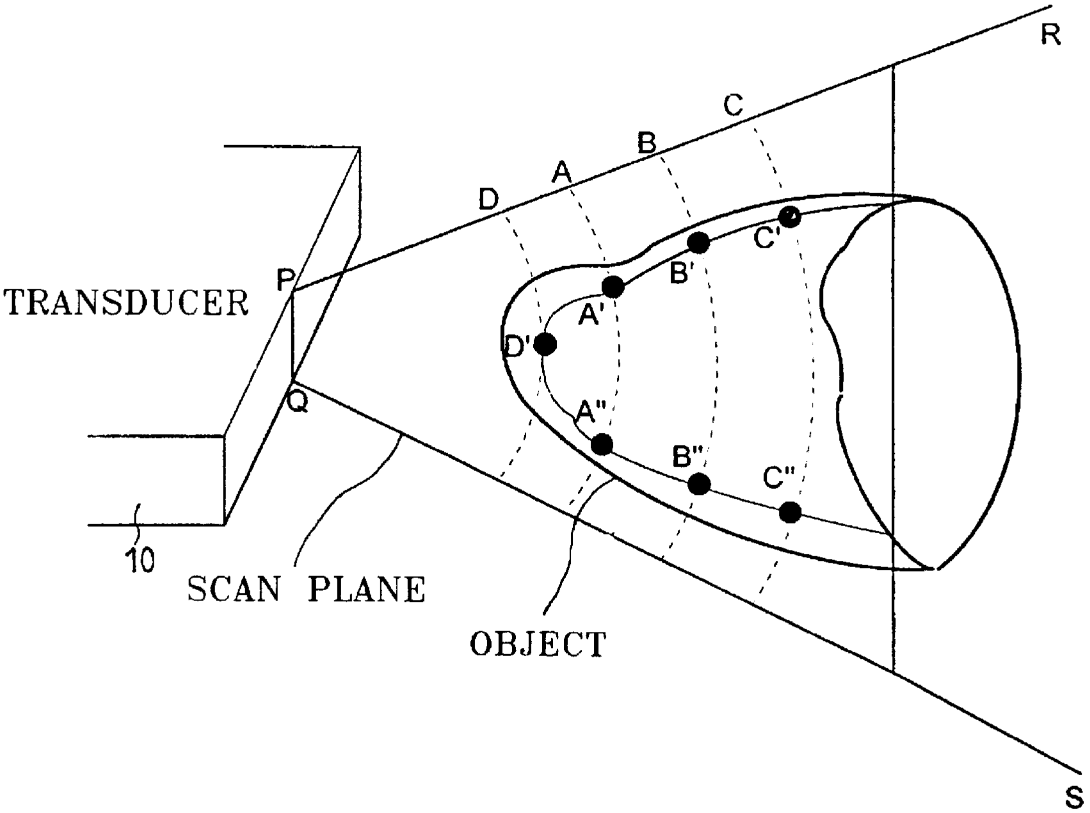
FIG. 6 (PRIOR ART)

Hereinafter, the operation of the ultrasonic three-dimensional imaging apparatus using a frequency spectrum according to the present invention will be described with reference to FIGS. 9 and 10A through 10C. The sub-elements of the transducer 200 generates an ultrasonic beam having a respectively different center frequency $f_0$ and converts an ultrasonic echo signal returning from the object into an electrical signal. The amplifier 20 amplifies the ultrasonic echo signal returning from the transducer 200. The TGC 30 varies a gain of the signal applied from the amplifier 20 according to time, and compensates an attenuation with respect to an ultrasonic reception distance. The beam former 40 performs a receive focusing. The analog-to-digital converter 50 converts the ultrasonic echo signal applied from the beam former 40 into digital data. The spectrum analyzer 110 segments the digital data applied from the analog-to-digital converter 50 according to time and analyzes the spectrum of each segment. Here, the segmentation of the digital data according to time is performed so that the data on the adjacent two segments is overlapped. Preferably, the segmentation is performed so that half of the data on two segments is overlapped. Also, it is possible that the segmentation is performed so that the data on two segments is not overlapped. As the segment gets longer, it becomes easier to analyze the spectrum. Thus, a resolution gets better in the elevational direction while it gets worse in the axial direction. Accordingly, a proper resolution adjustment is needed. The spectrum analyzer 110 outputs an image along an arc (formed by the targets of FIG. 6) on the scan plane determined by the transmitter 5 and the beam former 40. Such an image is obtained by the sufficient number of the segments obtained in the spectrum analyzer 110, with respect to the one plane via a one-time transmission and reception. The spectrum analyzer 110 outputs the spatial information gathered by repeating the above-described imaging procedures, to the 3-D reconstruction portion 130. The 3-D reconstruction portion 130 processes the obtained data. The 3-D reconstruction portion 130 extracts a shape of the surface of the object in a scan volume, and can modify to show an image of the extracted shape viewed at a predetermined position assuming that an illumination is incident at a designated angle.

While only certain embodiments of the invention have been specifically described herein, it will be apparent that numerous modifications may be made thereto without departing from the spirit and scope of the invention.

What is claimed is:

1. An area transducer array including: a plurality of linearly arranged transducer elements, each element being further divided vertically into a plurality of sub-elements, each sub-element adapted for independent operation along an elevational arc so as to perform three dimensional (3D) electronic scanning, each sub-element having different respective center frequencies and being arranged on a plane of each element determined by an elevational direction and a scanning direction in the form of a variable ultrasonic launching direction, each sub-element simultaneously transmitting at its assigned center frequency at its prescribed scanning direction to form a single composite beam which varies in an elevational scan direction for determining the elevational direction of particular targets associated with an object to be scanned.

2. The element arranging structure according to claim 1, wherein the center frequency assigned to each sub-element forms a beam whose center frequency continuously or gradually varies in the elevational direction.

3. An ultrasonic three-dimensional imaging apparatus comprising:

an area transducer array including a plurality of linearly arranged transducer elements, each element being vertically subdivided into a plurality of sub-elements, each sub-element adapted for independent operation along an elevational arc so as to perform three dimensional (3D) electronic scanning, each sub-element being assigned a unique center frequency;

an ultrasonic signal processor for receiving and focusing an ultrasonic echo signal received from an object via a predetermined time delay and converting it into a digital ultrasonic signal; and a frequency analysis unit for analyzing a frequency spectrum of the digital ultrasonic signal applied from said ultrasonic signal processor, gathering spatial information from each sub-element, and signal-processing the spatial image information received from each sub-element to discern a plurality of targets from a scanned object located at the same distance, and displaying the gathered image information.

4. The ultrasonic three-dimensional imaging apparatus according to claim 3, wherein said frequency analysis unit comprises:

a spectrum analyzer for segmenting the ultrasonic data input from said ultrasonic signal processor by time, repeatedly estimating the frequency spectrum of each segment forming the scan line, and outputting spatial image information; and a three-dimensional recalculation portion for receiving the spatial image information from said spectrum analyzer, and performing a predetermined operation to be displayed in a desired format.

5. The ultrasonic three-dimensional imaging apparatus according to claim 4, wherein said spectrum analyzer segments the ultrasonic data by time such that half the adjacent two segment data is overlapped.

6. The ultrasonic three-dimensional imaging apparatus according to claim 4, wherein said spectrum analyzer outputs a frequency spectrum corresponding to an image obtained along an arc on a scan plane in which targets exist.

* * * * *